United States Patent
Golshenas

(10) Patent No.: US 9,514,322 B2
(45) Date of Patent: Dec. 6, 2016

(54) BLOOD TREATMENT SYSTEM, MACHINE, AND METHOD WITH USER INTERFACE BLOCKING AND UNBLOCKING

(75) Inventor: Arash Golshenas, Malmo (SE)

(73) Assignee: Gambro Lundia AB, Lund (SE)

( * ) Notice: Subject to any disclaimer, the term of this patent is extended or adjusted under 35 U.S.C. 154(b) by 93 days.

(21) Appl. No.: 13/583,726

(22) PCT Filed: May 20, 2011

(86) PCT No.: PCT/EP2011/058285
§ 371 (c)(1),
(2), (4) Date: Oct. 3, 2012

(87) PCT Pub. No.: WO2011/144747
PCT Pub. Date: Nov. 24, 2011

(65) Prior Publication Data
US 2013/0205407 A1    Aug. 8, 2013

Related U.S. Application Data

(60) Provisional application No. 61/346,935, filed on May 21, 2010.

(30) Foreign Application Priority Data

May 21, 2010 (SE) .................... 1050507-1

(51) Int. Cl.
*G06F 21/62* (2013.01)
*A61M 1/16* (2006.01)
*G06F 19/00* (2011.01)

(52) U.S. Cl.
CPC ............ *G06F 21/6218* (2013.01); *A61M 1/16* (2013.01); *G06F 19/3481* (2013.01); *A61M 2205/505* (2013.01)

(58) Field of Classification Search
CPC ............... A61M 1/16; A61M 2205/505; G06F 19/3481; G06F 21/6218; G06F 21/10; G06F 21/31; G06F 2221/2141; G06F 9/4446; G06F 3/0481; G06F 3/04895; G06F 3/04886; G06F 17/30873; G06F 17/3089; G06F 3/04812; H04L 63/102; G06Q 10/10
(Continued)

(56) References Cited

U.S. PATENT DOCUMENTS 4,402,420 A * 9/1983 Chernack .............. A61J 1/1412
215/253
5,062,775 A * 11/1991 Orth ........................ A61M 1/10
417/319
(Continued)

FOREIGN PATENT DOCUMENTS

DE    102006054872 A1    5/2008
WO    WO 2005/031628 A1    4/2005
(Continued)

OTHER PUBLICATIONS

Chinese Office Action issued Sep. 29, 2014 for Patent Application No. 201180025233.1. English translation included (8 pages).
(Continued)

*Primary Examiner* — Kieu Vu
*Assistant Examiner* — Alvaro R Calderon, IV
(74) *Attorney, Agent, or Firm* — Mueting, Raasch & Gebhardt, P.A.

(57) ABSTRACT

A user interface (21) for an extracorporeal blood treatment machine is provided, as well as a system (200) for feedback control of a user. The system (200) comprises a controller (22), a sensor (108) and a device (107) for administration of a substance. The controller (22) is enabled to receive input from the user interface and send instructions to the user
(Continued)

interface and the controller is arranged to control the operation of the device (107) for administration of a substance. The device (107) for administration of a substance is monitored by the sensor (108) and the controller (22) is enabled to receive input from the sensor (108) such that the controller is enabled to provide feedback to the user interface by said instructions. A method (40) for performing a critical action in a system (200) is also provided.

17 Claims, 6 Drawing Sheets

(58) Field of Classification Search
USPC .......................... 726/28; 715/705, 741–747
See application file for complete search history.

(56) References Cited

U.S. PATENT DOCUMENTS

| | | | | |
|---|---|---|---|---|
| 5,366,896 | A * | 11/1994 | Margrey | G01N 35/00871 422/105 |
| 5,573,502 | A * | 11/1996 | LeCocq | A61M 1/3664 128/DIG. 3 |
| 5,591,344 | A * | 1/1997 | Kenley | A61L 2/04 210/134 |
| 5,609,770 | A * | 3/1997 | Zimmerman | A61M 1/16 210/143 |
| 5,620,608 | A * | 4/1997 | Rosa | G06F 19/3406 210/143 |
| 6,361,518 | B1 | 3/2002 | Brierton | |
| 7,294,312 | B2 * | 11/2007 | Green | B01L 9/00 422/561 |
| 7,410,475 | B2 * | 8/2008 | Krensky et al. | 604/29 |
| 7,494,590 | B2 * | 2/2009 | Felding et al. | 210/646 |
| 2002/0065467 | A1 * | 5/2002 | Schutt | A61B 5/055 600/454 |
| 2002/0095673 | A1 * | 7/2002 | Leung et al. | 725/25 |
| 2003/0220605 | A1 * | 11/2003 | Bowman et al. | 604/29 |
| 2004/0010207 | A1 * | 1/2004 | Flaherty | A61B 5/14532 600/573 |
| 2004/0167465 | A1 * | 8/2004 | Mihai et al. | 604/67 |
| 2004/0176667 | A1 * | 9/2004 | Mihai et al. | 600/300 |
| 2004/0267340 | A1 * | 12/2004 | Cioanta | A61F 7/123 607/105 |
| 2005/0070837 | A1 * | 3/2005 | Ferrarini et al. | 604/5.01 |
| 2005/0113754 | A1 * | 5/2005 | Cowan | A61M 5/14546 604/131 |
| 2005/0148867 | A1 * | 7/2005 | Neer | A61M 5/14546 600/431 |
| 2005/0182322 | A1 * | 8/2005 | Grispo | A61M 5/36 600/432 |
| 2005/0182323 | A1 * | 8/2005 | Grispo | A61M 5/36 600/432 |
| 2005/0234382 | A1 * | 10/2005 | Tonelli | A61M 5/1456 604/4.01 |
| 2005/0234387 | A1 * | 10/2005 | Tonelli | A61M 1/3672 604/6.07 |
| 2005/0256444 | A1 * | 11/2005 | O'Mahony et al. | 604/5.02 |
| 2006/0058774 | A1 * | 3/2006 | Delnevo et al. | 604/500 |
| 2006/0132447 | A1 * | 6/2006 | Conrad | 345/168 |
| 2007/0023334 | A1 * | 2/2007 | Hallstadius et al. | 210/94 |
| 2007/0138069 | A1 * | 6/2007 | Roncadi et al. | 210/96.2 |
| 2007/0185429 | A1 * | 8/2007 | O'Mahony et al. | 604/4.01 |
| 2008/0027368 | A1 * | 1/2008 | Kollar | A61M 1/3621 604/6.14 |
| 2008/0046115 | A1 * | 2/2008 | Tabellion et al. | 700/226 |
| 2008/0077069 | A1 * | 3/2008 | O'Mahony et al. | 604/6.11 |
| 2008/0209357 | A1 * | 8/2008 | Vasta et al. | 715/771 |
| 2008/0234620 | A1 * | 9/2008 | Tonelli et al. | 604/5.01 |
| 2009/0030366 | A1 * | 1/2009 | Hochman | A61M 5/20 604/67 |
| 2009/0043253 | A1 * | 2/2009 | Podaima | G06F 19/322 604/67 |
| 2009/0082684 | A1 * | 3/2009 | Sornmo et al. | 600/513 |
| 2009/0113335 | A1 * | 4/2009 | Sandoe et al. | 715/773 |
| 2009/0118594 | A1 * | 5/2009 | Zdeblick | A61B 5/117 600/300 |
| 2009/0149743 | A1 * | 6/2009 | Barron | A61M 5/007 600/431 |
| 2009/0163860 | A1 * | 6/2009 | Patrick | A61M 19/00 604/83 |
| 2009/0222119 | A1 * | 9/2009 | Plahey et al. | 700/94 |
| 2009/0241072 | A1 * | 9/2009 | Chaudhri et al. | 715/863 |
| 2010/0049114 | A1 | 2/2010 | Brown | |
| 2010/0076364 | A1 * | 3/2010 | O'Mahony et al. | 604/6.11 |
| 2010/0175483 | A1 * | 7/2010 | O'Mahony et al. | 73/754 |
| 2011/0016392 | A1 * | 1/2011 | Humeniuk | A61M 5/14546 715/705 |
| 2011/0036768 | A1 * | 2/2011 | Ueda | A61M 1/16 210/321.71 |
| 2011/0061765 | A1 * | 3/2011 | Hartman | B65B 3/003 141/2 |
| 2011/0071465 | A1 * | 3/2011 | Wang et al. | 604/67 |
| 2011/0098635 | A1 * | 4/2011 | Helmore et al. | 604/29 |
| 2011/0125085 | A1 * | 5/2011 | McGill et al. | 604/29 |
| 2011/0163030 | A1 * | 7/2011 | Weaver | A61M 1/3627 210/637 |
| 2011/0166521 | A1 * | 7/2011 | Marshall | A61M 5/20 604/135 |
| 2011/0245762 | A1 * | 10/2011 | Crank | A61M 5/1413 604/68 |
| 2012/0065482 | A1 * | 3/2012 | Robinson et al. | 600/309 |
| 2012/0138533 | A1 * | 6/2012 | Curtis | A61M 1/16 210/646 |

FOREIGN PATENT DOCUMENTS

| | | |
|---|---|---|
| WO | WO 2007/023328 A1 | 3/2007 |
| WO | WO 2007/062315 A2 | 5/2007 |
| WO | WO 2008/074316 A2 | 6/2008 |
| WO | WO 2008/074316 A3 | 6/2008 |
| WO | WO 2009/156806 | 12/2009 |

OTHER PUBLICATIONS

Communication Pursuant to Article 94(3) EPC for Application No. 11720534.4-1651 dated May 30, 2016 (6 pages).

* cited by examiner

BLOOD TREATMENT SYSTEM, MACHINE, AND METHOD WITH USER INTERFACE BLOCKING AND UNBLOCKING

This application is a U.S. National Stage Application of International Application No. PCT/EP2011/058285, filed May 20, 2011, which was published in English on Nov. 24, 2011 as International Patent Publication No. WO 2011/144747 A1, and which claims the benefit under 35 U.S.C. 119(e) of U.S. Provisional Application No. 61/346,935, filed May 21, 2010. International Application No. PCT/EP2011/058285 also claims priority to Swedish Application No. 1050507-1, filed May 21, 2010.

TECHNICAL FIELD

This invention pertains in general to the field of machines for extracorporeal blood treatment. More particularly the invention relates to a user interface for a machine for extracorporeal blood treatment, a method to be run on a machine for extracorporeal blood treatment as well as to a machine for extracorporeal blood treatment comprising the user interface.

Specifically, though not exclusively, the invention is usefully applied in the field of dialysis machines, such as for example machines for intensive treatment for acute renal failure.

BACKGROUND

User interfaces in machines for extracorporeal blood treatment generally have the function of setting up a dialog, i.e. an interaction, between the processor of the machine and the user or operator using the machine, for example in order to prime the machine, regulate machine operation or for setting desired treatment parameters, such as, for example, blood pump flow rate, the flow rate and temperature of the dialysis fluid, treatment times, and so on.

Especially important is the interaction between the user or operator and the machine during preparation procedures prior to the actual treatment and preparation procedure during treatment, such as change of syringe and/or change of fluid bag, since these procedures can be very long, complicated and laborious.

Generally when going from one stage to another, e.g. going from priming to treatment mode, the user has to interact with the machine. The possibility of doing mistakes during these interactions should be minimized.

Normally these preparation procedures comprise at least the mounting of the disposable set onto the machine. The disposable set usually comprises at least the extracorporeal blood circuit, destined in use to be connected to a vascular access of the patient about to undergo treatment, and the blood treatment unit, generally comprising a filtration unit, for example a dialyzer.

Treatment preparations procedures usually further comprise at least one priming stage for the circuit and the blood treatment unit, as well as a connection stage of the extracorporeal circuit to the vascular access of the patient.

A user interface for a machine for extracorporeal blood treatment has been disclosed in WO 2005/031628 A1. Here, the user interface comprises a touch screen, a memory containing at least two images and a controller. The controller is programmed for displaying on a screen of the touch screen a display including at least two distinct areas, a first area of the two distinct areas exhibiting at least two touch keys and a second area exhibiting a first of the at least two images.

By selecting a touch key, a user will instruct the controller to display a corresponding image. The image may aid the user in performing operations in relation to the machine for extracorporeal blood treatment, such as during priming.

However, the preparation procedures can be very long, complicated and laborious, especially with intensive therapy dialysis machines, where the machine operator is often not specialized in the use of these apparatuses, and where the time factor is critical as the patient is often in quite a serious condition and needs as fast an intervention as possible.

Hence, an improved user interface for machines for extracorporeal blood treatment would be advantageous, and in particular a user interface allowing for easier use, increased safety and/or speed of operation would be advantageous.

SUMMARY

Accordingly, the present invention preferably seeks to mitigate, alleviate or eliminate one or more of the above-identified deficiencies in the art and disadvantages singly or in any combination and solves at least the above mentioned problems by providing a user interface, a machine and a method according to the appended patent claims.

The general solution according to the invention is to apply a sensor to provide feedback information to the controller regarding an option selected by the user.

More particularly, the controller is programmed to inhibit any other options selectable by the user until the sensor feedback information is received.

According to one aspect of the invention, a user interface for an extracorporeal blood treatment machine is provided. The user interface comprises at least one screen (16), at least one memory comprising at least two images, at least a controller and at least one key (17). The controller is programmed for detecting activation of the at least one key (17), displaying on the screen (16) a first image which in the memory is assigned to the activated key (17). The controller is further programmed for blocking the user interface until a first signal is received and upon receipt of the first signal, unblocking the user interface (21), and displaying on the screen (16) a second image.

According to another aspect, a system (200) for feedback control of a user interface according an aspect is provided. The system (200) comprises a controller (22), a sensor (108) and a device (107) performing an operation on a machine for extracorporeal blood treatment. Throughout the disclosure, the operation is exemplified as administration of a substance. However, it is provided that any kind of device (107) performing an operation on a machine for extracorporeal blood treatment may be used. The controller (22) is enabled to receive input from the user interface and send instructions to the user interface and the controller is arranged to control the operation of the device (107) for administration of a substance. The device (107) for administration of a substance is monitored by the sensor (108) and the controller (22) is enabled to receive input from the sensor (108) such that the controller is enabled to provide feedback to the user interface by said instructions.

According to a further aspect, a machine for extracorporeal blood treatment is provided. The machine comprises at least one blood pump, at least one housing zone for receiving at least one extracorporeal blood circuit in a position wherein the at least one extracorporeal blood circuit is operatively associated with the blood pump. The machine further comprises at least a machine controller and at least one user interface according to an aspect of the invention, for dialogue between an operator and the machine controller.

According to another aspect, a method (40) for performing a critical action in a system according to an aspect is provided. The method comprises the steps of blocking (41) the user interface (21), detecting (42) a first signal from the sensor (108) associated with the critical action and unblocking (43) the user interface when the first signal is detected.

According to yet a further aspect, a computer-readable medium, having embodied thereon a computer program for processing by a computer is provided, wherein the computer program comprises code segments for performing each of the steps of the method according to an aspect.

The present invention has the advantage over the prior art that it improves safety by reducing the probability of error when preparing an apparatus for extracorporeal blood treatment.

A further advantage of the invention is to provide a machine for extracorporeal blood treatment in which the preliminary operations in preparation for a correct functioning of the machine are easy for the user to accomplish, even where the latter is not specialized.

A further advantage of the invention is that it enables rapid learning, as well as rapid execution even by a non-expert user, of the procedural steps necessary for preparation of the machine for extracorporeal blood treatment.

A further advantage of the present invention is to provide a user interface which is easy to use, and by means of which times for carrying out the preliminary stages of machine preparation for extracorporeal blood treatment can be reduced-for example, in relation to the mounting of the single-use parts of the apparatus on the machine.

A further advantage is that the expert users that are used to the preparation procedure will not be restricted in terms of rapid mounting and/or extra confirmations screen.

Further embodiments of the invention are defined in the dependent claims.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DESCRIPTION OF EMBODIMENTS

Several embodiments of the present invention will be described in more detail below with reference to the accompanying drawings in order for those skilled in the art to be able to carry out the invention. The invention may, however, be embodied in many different forms and should not be construed as limited to the embodiments set forth herein. Rather, these embodiments are provided so that this disclosure will be thorough and complete, and will fully convey the scope of the invention to those skilled in the art. The embodiments do not limit the invention, but the invention is only limited by the appended patent claims. Furthermore, the terminology used in the detailed description of the particular embodiments illustrated in the accompanying drawings is not intended to be limiting of the invention.

The following description focuses on an embodiment of the present invention applicable to a machine for extracorporeal blood treatment and in particular to a dialysis machine or monitor. However, it will be appreciated that the invention is not limited to this application but may be applied to many other medical devices including for example infusion pumps, peristaltic pumps, liver treatment devices, or ultra filtration devices.

Machine Parts

Figure 1:
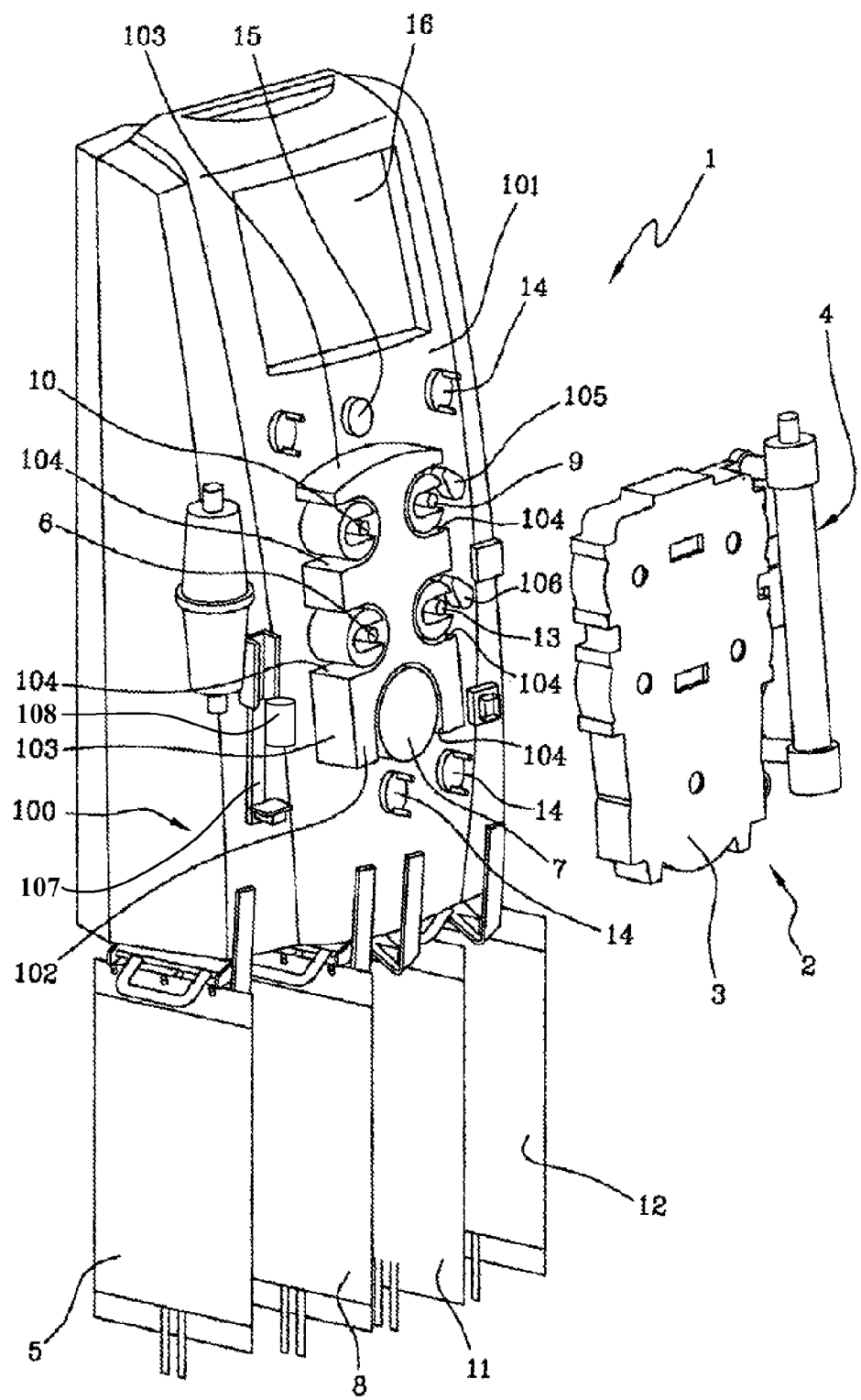
FIG. 1 is an illustration of a machine for extracorporeal blood treatment according to an embodiment.

In an embodiment according to FIG. 1, 1 denotes in its entirety a machine for extracorporeal blood treatment, represented in the illustrated embodiment by a dialysis machine which is suitable for intensive treatment of acute kidney failure. 2 denotes in its entirety an integrated module which can be coupled to the dialysis machine 1.

The integrated module 2 is constituted by a combination of at least one support element 3 of a distribution circuit (of known type and not illustrated) arranged on the support element 3, and a blood treatment unit 4. The blood treatment unit 4 can be, for example, a plasma filter, a hemodialysis filter, a hemofiltration filter, or a different unit.

The hydraulic circuit, which is completed by a combination of the integrated module 2 and the machine 1, comprises a blood circuit which removes blood from a patient, for example via a catheter inserted in a vascular access of the patient, and takes the blood though a blood removal line to the treatment unit 4.

The blood passes through a first chamber (blood chamber) of the treatment unit 4 and, via a return line, is transported back to the patient.

Immediately downstream of the blood removal zone, connection is made between the removal line and an auxiliary pre-infusion line.

In particular, the machine includes at least one container of a first sterile fluid 5 for supplying the pre-infusion line; fluid transport means, in the embodiment constituted by a pre-infusion pump 6, for example a peristaltic pump, control the flow of fluid in the pre-infusion line directly into the blood via a direct connection to the blood removal line.

Generally the container of the first sterile fluid 5 can contain a pre-infusion fluid, although the same container can be used for containing an anticoagulant, usually of a locally-acting type.

The machine further comprises means for transporting fluid, i.e. in the embodiment at least one blood pump 7 for control and management of a correct blood flow in the circuit. The blood pump 7 is peristaltic.

Once a blood circulation direction has been established from the blood removal zone to the blood treatment unit 4, and thereafter to the blood return line towards the patient, a blood pressure sensor is included immediately downstream of the auxiliary pre-infusion line.

Continuing along the blood circulation direction, a device 107 is included for administration of a substance such as an anticoagulant or calcium, for example a syringe containing appropriate doses of heparin, operably connected to a pump for filling/emptying the syringe. The device 107 may also be a scale or a pressure gauge. In an embodiment, the device 107 infuses heparin, i.e. is a heparin infusion device.

In an embodiment, several devices 107 may be included for independent administration of several substances.

The blood then crosses a further pressure sensor which monitors the correct flow rate internally of the blood circuit.

After crossing the first blood chamber of the treatment unit 4, where substance-exchange and molecular and fluid exchange takes place through a semi-permeable membrane, the treated blood enters the return line, crossing a gas separator (generally air), where any air bubbles present or introduced to the blood during treatment are expelled.

The treated blood exiting from the gas separator (also known as a deaeration chamber) crosses a bubble sensor (also known as an air detector) which checks that these dangerous formations are not present in the treated blood, which is about to be sent back into the blood circuit of the patient.

Immediately downstream of the bubble sensor a closure element is located, which on activation of an alarm can block the blood flow towards the patient. In particular, if the bubble sensor reveals the presence of anomalies in the blood flow, the machine, by means of the closure element (which can be a cock, a clamp or the like) the blood passage would immediately be stopped in order to prevent any kind of consequence to the patient. Downstream of the closure element the treated blood is returned to the patient undergoing treatment.

The distribution circuitry comprises a first circuit of a second sterile fluid (dialyzing liquid) having at least one inlet line to the blood treatment unit 4 and an outlet line from the treatment unit 4.

At least one container of the second sterile fluid 8 is destined to supply the inlet line of the first circuit.

The inlet line is destined to cooperate with means for fluid transport, being at least one pump 9 (in the embodiment a peristaltic pump) predisposed on the frontal part of the machine to control the flow of the second sterile fluid coming from the container 8, and to define a circulation direction. Downstream of the pump 9 of the second sterile fluid, along the circulation direction, a branch is included which divides the first circuit of the second sterile fluid into an inlet branch and an infusion branch.

In particular the infusion branch is connected to the blood circuit return line. In other words, with this infusion line infusion can be made directly into the blood, using the contents of the container 8 of the second sterile fluid.

The inlet branch takes the second sterile fluid directly to the blood treatment unit 4, in particular to a second chamber (dialysis chamber) of the unit 4.

The first circuit of the second sterile fluid is further associated to a first selector which determines the percentage quantities of fluid flow into the infusion branch and the inlet branch.

Generally the first selector, usually located in proximity of the branch, enables selection between at least a first operative condition, in which the second sterile fluid can pass into the inlet branch but cannot pass into the infusion branch, and a second operative condition, in which they allow passage of fluid into the infusion branch but not into the inlet branch. In other words the first selector can be constituted by a valve element suitable for operating in a fluid circuit, which can alternatively shut off passage of fluid into one or the other branch. Selectors can be used, if preferred, which can decide prior to starting the quantity of the second sterile fluid which can pass at a same time into one and the other branch. Otherwise the percentage amounts of fluid passing into one branch or the other can be established according to determined times and therapies.

The second sterile fluid (dialyzing liquid) crosses the inlet branch and enters the second chamber (dialysis side) of the blood treatment unit 4.

In particular the first chamber (blood chamber), crossed by the blood flow, is separated from the second chamber (dialysis chamber), crossed by the second sterile fluid, by a semi-permeable membrane which enables passage of the damaging molecules and substances and fluids in the blood towards the second sterile fluid (dialyzing liquid), mainly through convection and diffusion processes; at the same time, and by the same principles, passage of substances and molecules from the second sterile fluid and towards the blood is allowed.

The second sterile fluid, for dialysis, enters the outlet line of the first circuit and crosses a special pressure sensor for controlling the functioning of the line. Means for transporting the fluid, for example an effluent drainage pump 10, are present, which control the flow in the fluid circuit outlet line. This pump 10, as the others, is usually peristaltic.

The discharge fluid then crosses a blood leak detector 15 and is sent on to an effluent collection container 11.

An infusion line is located on the return line of the blood circuit. In particular, a third sterile fluid (infusion fluid) is sourced from at least one auxiliary container 12 and, by action of a fluid transport means, generally an infusion pump 13 which controls flow (in the embodiment a peristaltic pump), is sent directly to the blood circuit return line.

The third sterile fluid (infusion liquid) can be sent directly into the gas separator device.

The post-infusion branch of the first circuit of the second sterile fluid and the infusion line of the third sterile fluid are provided with a common terminal inlet tract to the blood circuit. The terminal inlet tract is located downstream of the infusion pump 13 with respect to an infusion direction, and sends the fluid directly into the gas separator. At least one pre-infusion branch is present in the infusion line, connected to the blood circuit removal line.

In more detail, there is a branch located downstream of the infusion pump 13 with respect to the infusion direction, which divides the infusion line into a pre-infusion branch and a post-infusion branch.

The pre-infusion branch takes the fluid removed from the container to the blood circuit removal line downstream of the blood pump 7 (downstream with respect to the circulation direction). The post-infusion branch is directly connected to the common terminal tract.

The infusion line further comprises a second selector for determining the percentage quantities of liquid flow to send into the post-infusion branch and the pre-infusion branch. The second selector, located in proximity of the branch, is positionable between at least one first operative configuration, in which fluid can pass into the pre-infusion branch but not the post-infusion branch, and at least a second operative configuration, in which fluid is allowed to pass into the post-infusion branch and not the pre-infusion branch.

As with the first selector on the first circuit of the second sterile fluid, the second selector is able to establish percentages of fluid passing into each of the two branches, and can if necessary vary the times according to the treatments to be carried out. The first and second selectors are usually, but not necessarily, of similar type.

The machine is provided with means for determining at least the weight of the container of the first sterile fluid 5 and/or the container of the second sterile fluid 8 and/or the container of the third sterile fluid 12 and/or the discharge container 11. The means for determining are constituted by weight sensors, for example scales (at least one independent scales for each container or fluid bag associated to the machine).

There will be at least four of these scales present, each independent of the others, and each predisposed to measure the respective weight of a container 5, 8, 11, 12.

There is also a CPU (not shown) which is active on, the blood circuit and in particular on the pressure sensor, the blood pump 7, the device 107 for administration of a substance, the further pressure sensor, as well as on the bubble sensor and the closure element.

The CPU is also used for controlling the first circuit of the second sterile fluid, and in particular to receive data sent by the scales relating to the weight of the container 8; it is also active on the pump 9, the first selector, the pressure sensor, the drainage pump 10 and the scales weighing the effluent discharge container 11.

The CPU is also active on the infusion line of the third sterile fluid, monitoring the weight of the container 12 (measured by a scales), and also controls the infusion pump 13 and the second selector.

Finally, the CPU is active on the auxiliary line for pre-infusion of the first sterile fluid, measuring the weight of the container 5 via scales and commanding the pre-infusion pump 6 according to the treatment to be carried out.

The above, purely descriptive, account of the hydraulic circuitry of the machine for extracorporeal blood treatment will now be followed by a brief explanation of how the device functions.

Before the actual treatment begins, the apparatus must be prepared. The whole hydraulic circuitry and the treatment unit are correctly associated to the machine so that the various peristaltic pumps engage the respective tracts of tubing, and all the sensors are correctly positioned; also, the relative bags containing the various fluids are joined up to the respective supply or receiving lines of the liquids, and the blood circuit is connected up to an artery or vein of the patient. When set-up is complete, an initial circulation of the blood internally of the respective circuit is made.

According to the type of treatment selected (pure ultra-filtration, hemodialysis, hemofiltration, hemodiafiltration, etc.), the machine for extracorporeal blood treatment is automatically activated and controlled by the processing unit.

The machine 1 exhibits a machine body 100 provided, on a front surface 101 thereof, with peristaltic pumps 6, 7, 9, 10, 13, destined to cooperate in use with respective tracts of U-shaped tubing on the integrated module.

The machine body 100 exhibits a relief acting as a positioning guide 102 which projects from the front surface 101, which is complementarily shaped with respect to the support element 3 with which it will couple in use.

In other words, the guide 102 exhibits a lateral surface 103 which, when the integrated module is coupled thereto, is contained within a perimeter wall of the support element 3.

The peristaltic pumps also project from the front surface 101 of the machine body 100 and at least a part of the lateral surface of the pumps is complementarily shaped with respect to the perimeter wall of the support element 3.

The projecting peristaltic pumps and the guide 102 in combination define seatings 104 having a semicircular shape, i.e. a U-shape, which seatings 104 are destined to receive the corresponding tracts of U-shaped tubing of the circuitry.

A first mobile element 105 and a second mobile element 106, substantially identical and borne directly on the machine body 100, are destined to be active on the infusion and/or inlet branch of the second sterile fluid (the first mobile element 105) and, respectively, on the pre-infusion branch and/or the post-infusion branch of the third sterile fluid (the second mobile element 106). In particular the first and second selectors can be constituted by the mobile elements 105, 106, destined to be controlled by the CPU to selectively allow or block passage of fluid into one or another of the branches.

The front surface of the machine further exhibits a plurality of fastening elements 14 for fixing the pressure sensors; the pressure sensors associated to the circuitry of the integrated module are hereat connected up to the CPU.

The blood leak detector 15 is also predisposed on the front surface of the machine, and during the apparatus preparation process is associated to the fluid circuit in outlet from the treatment unit 4.

A sensor 108 is located in proximity to the device 107 for administration of a substance, so that the sensor may measure parameters related to the device 107 for administration of a substance.

In an embodiment, multiple sensors 108 are located either integrated in the device 107 for administration of a substance and/or in the proximity to the device 107 for administration of a substance, so that the sensors may measure single or multiple parameters related to the device 107 for administration of a substance.

Figure 2:
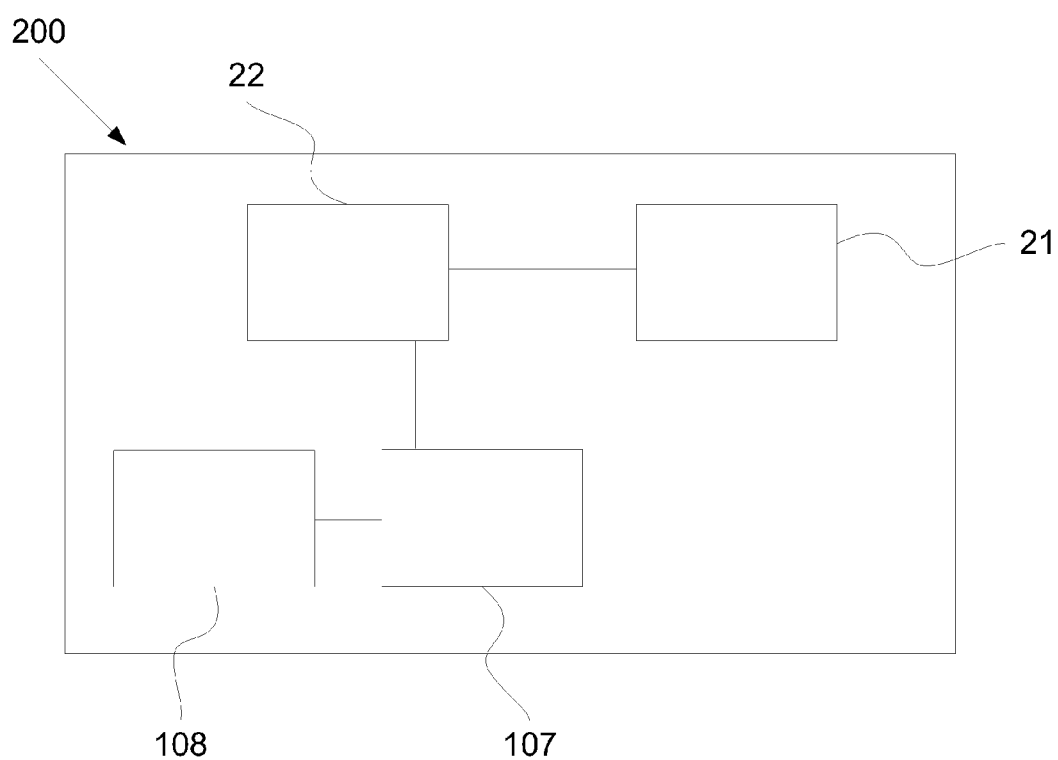
FIG. 2 is a block diagram schematically illustrating a system for feedback control of a user interface.

FIG. 2 discloses a system 200 for feedback control of a user interface 21, comprising a controller 22, such as the CPU, the sensor 108 as well as the device 107 for administration of a substance. The controller 22 may constitute a part of the user interface 21.

The user interface and the controller have here been described functionally for ease of understanding. However, in practice, the hardware and software implementing these functions are preferably implemented as an embedded computer system where boundaries are hard to define. For an artisan within embedded design, it is however clear from this disclosure how to implement the functionality.

The system 200 is configured so that the controller 22 may receive input from the user interface 21, as well as send instructions to the user interface 21. The controller also controls the operation of the device 107 for administration of a substance. Furthermore, the controller 22 receives input from the sensor 108, which is monitoring the device 107 for administration of a substance. The controller 22 may also send instructions to the sensor 108.

However, FIG. 2 should not be construed as limiting the ways in which the parts of the system may be connected. For example, in an embodiment where the sensor 108 is integrated in the device 107 for administration of a substance (not shown), the controller receives input from the sensor 108 via the device 107 for administration of a substance.

In an embodiment (not shown) one sensor 108 may send multiple signals to the controller 22 during different operational stages.

In an embodiment (not shown) multiple sensors 108 may send signals to the controller 22. The controller 22 may be configured to receive more than one signal before controlling the operation of the device 107. Alternatively, the controller 22 may be configured to control the operation of the device 107 according to different scenarios, depending on which of the multiple sensors 108 sends the signal.

The controller 22 may be any unit normally used for performing the involved tasks, e.g. a hardware, such as a processor with a memory. The processor may be any of a variety of processors, such as Intel or AMD processors, microprocessors, Programmable Intelligent Computer (PIC) microcontrollers, Digital Signal Processors (DSP), etc. However, the scope of the invention is not limited to these specific processors. The memory may be any memory capable of storing information, such as Random Access Memories (RAM) such as, Double Density RAM (DDR, DDR2), Single Density RAM (SDRAM), Static RAM (SRAM), Dynamic RAM (DRAM), Video RAM (VRAM), etc. The memory may also be a FLASH memory such as a USB, Compact Flash, SmartMedia, MMC memory, MemoryStick, SD Card, MiniSD, MicroSD, xD Card, TransFlash, and MicroDrive memory etc. However, the scope of the invention is not limited to these specific memories.

In an embodiment where the device 107 for administration of a substance is a syringe, the sensor 108 is a load sensor located so that the sensor registers the location of the syringe plunger. Thus, the sensor 108 registers whether the plunger is fully inserted and the syringe is substantially empty or if the plunger is fully extended and the syringe is substantially full.

In an embodiment, the sensor 108 is an optical sensor located so that the sensor may measure the content of the device 107 for administration of a substance. The sensor may then detect if there is air in the device 107. The sensor 108 may also detect the type of substance contained in the device 107 by absorbance measurements, well known to a person skilled in the art.

In an embodiment, the sensor 108 is an ultrasonic sensor. The sensor 108 may then detect if there is air in the device 107.

In an embodiment, the sensor 108 is a Hall Effect sensor. The sensor 108 may then detect displacement of parts of the device 107.

Figure 3:
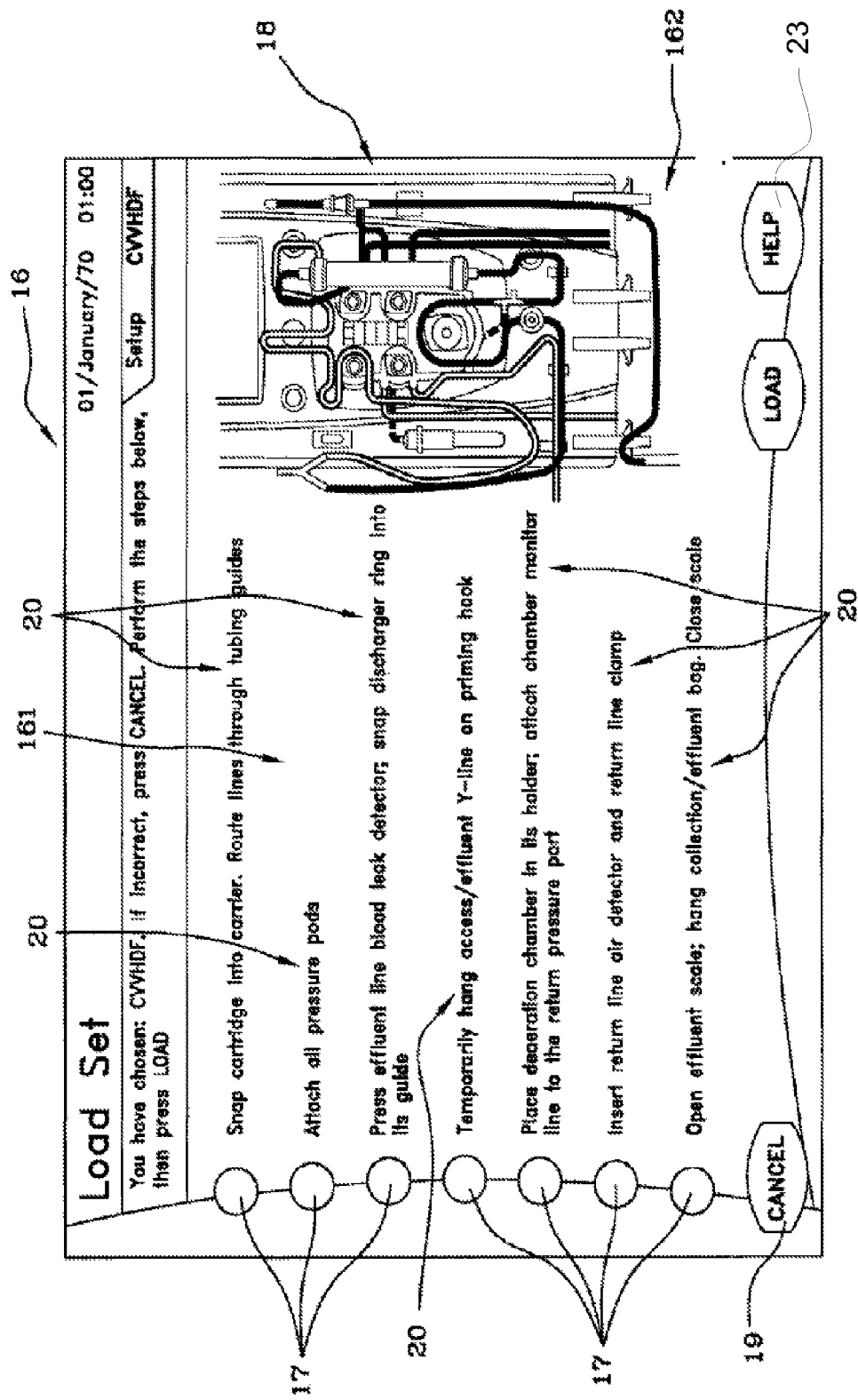
FIG. 3 is an example of a screen view of the user interface.

In FIG. 3, 16 denotes a screen, which is part of the machine user interface 21. The user interface comprises a touch screen and a controller programmed to display on the screen 16 of the touch-screen a plurality of displays in which the screen 16 is divided into two distinct areas.

In the present description, the term "touch screen" refers to a device having a screen for data output, which is also used for input through selection of parts (touch keys or soft keys) of the screened display using the fingers; the device is able to detect where a user has touched the screen and from this derive the selected commands and perform them.

It is however provided that the invention is not limited to an embodiment with a touch screen. Equally possible would be an embodiment with a monitor screen without touch function. In this case, the touch keys would be analog switch means, such as keys or buttons. When such analog switch means "appears", it is meant that it is highlighted, i.e. by a light means such as a diode.

In an embodiment where the screen is a touch screen, a touch key may be highlighted by a different visual appearance in relation to other touch keys, for instance to indicate a key enabled for activation by the user.

As is seen in FIG. 3, the two distinct areas of the screen 16 are a first area 161 (on the left in the figure) exhibiting a plurality of touch keys 17, and a second area 162 (on the right in the figure), by the side of the first area, selectively displays a plurality of pictographs 18, each of which is associated to one of the touch-keys 17.

After the operator has used the touch-screen to select the desired treatment (in the illustrated case hemodiafiltration, but which could variously be hemofiltration, hemodialysis, ultrafiltration, plasma exchange therapy etc.), the controller of the user interface is programmed to bring up on screen the display of FIG. 3, in which the indications relating to the steps the operator must perform to prepare the machine are shown. In this case the activity consists in mounting the disposable set, where the set comprises, as mentioned above, the support element 4 and relative circuitry, and the blood treatment unit 5. The data appearing on-screen comprises, in the example, an English expression viz "Load set", which is an instruction relating to the next steps to take.

The display also includes an indication of the selected treatment. In this case the treatment selected is hemodiafiltration, continuous venovenous haemodiafiltration, and the well-known English acronym for this is "CVVHDF".

The display comprises a touch key 19 for cancelling the treatment selection, if the operator judges it to be incorrect.

The touch keys 17 correspond to one or more procedural steps, arranged in top-down order according to temporal sequence for carrying out the steps necessary for loading a disposable set on the machine.

The first area 161 of the display has, by the side of each touch key 17, an alphanumeric indication or legend 20 describing in word form the procedural step or steps the operator must perform that are associated with the respective touch key 17.

A pictograph 18 appears in the second area 162 of the screen in this display, which pictograph 18 represents the front of the dialysis machine, with the disposable set already mounted on the machine. The pictograph 18 (FIG. 2) describes the fluid distribution circuitry using lines in colour code according to the type of fluid line represented, so that, for example, the blood removal line is represented by a red line, the blood return line is blue, the auxiliary pre-infusion line of the first sterile fluid is white, and so on.

On touching any one of the touch keys 17 the controller brings up a pictograph 18 in the second area of the display, corresponding to the instruction associated to the selected touch key 17.

If the action associated to the selected touch key 17 is critical for the operation of the machine 1, the system may be configured to restrict the options available to a user based on information provided by one or more sensors in the machine 1. The critical action may be a single action, or a combination of several critical actions performed sequentially, e.g. constituting a critical action pathway.

Figure 4A:
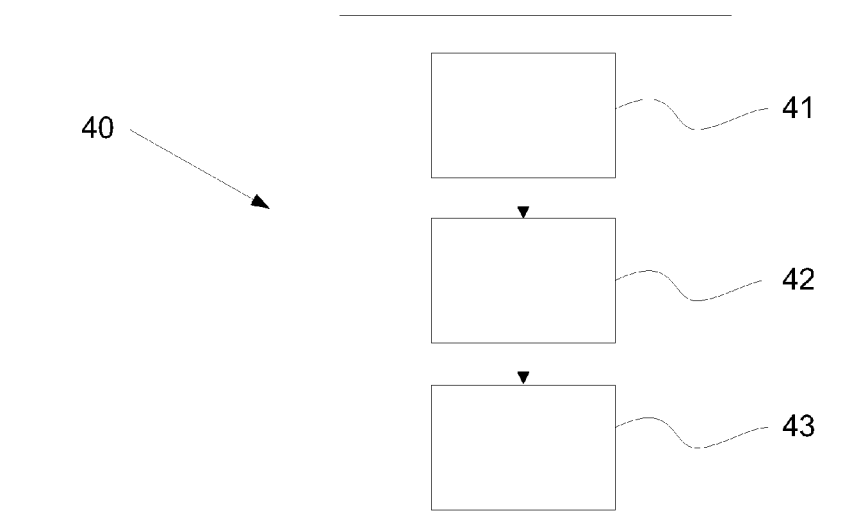
FIG. 4 illustrates flow charts schematically illustrating methods according to embodiments.

In an embodiment according to FIG. 4a, a method 40 for performing a critical action in a system according to some embodiments is provided, for instance in connection with preparation procedures prior to the actual treatment and preparation procedure during treatment. Said method comprises the steps of blocking 41 the user interface 21; detecting 42 a first signal from the sensor 108 associated with the critical action; and unblocking 43 the user interface.

Figure 4B:
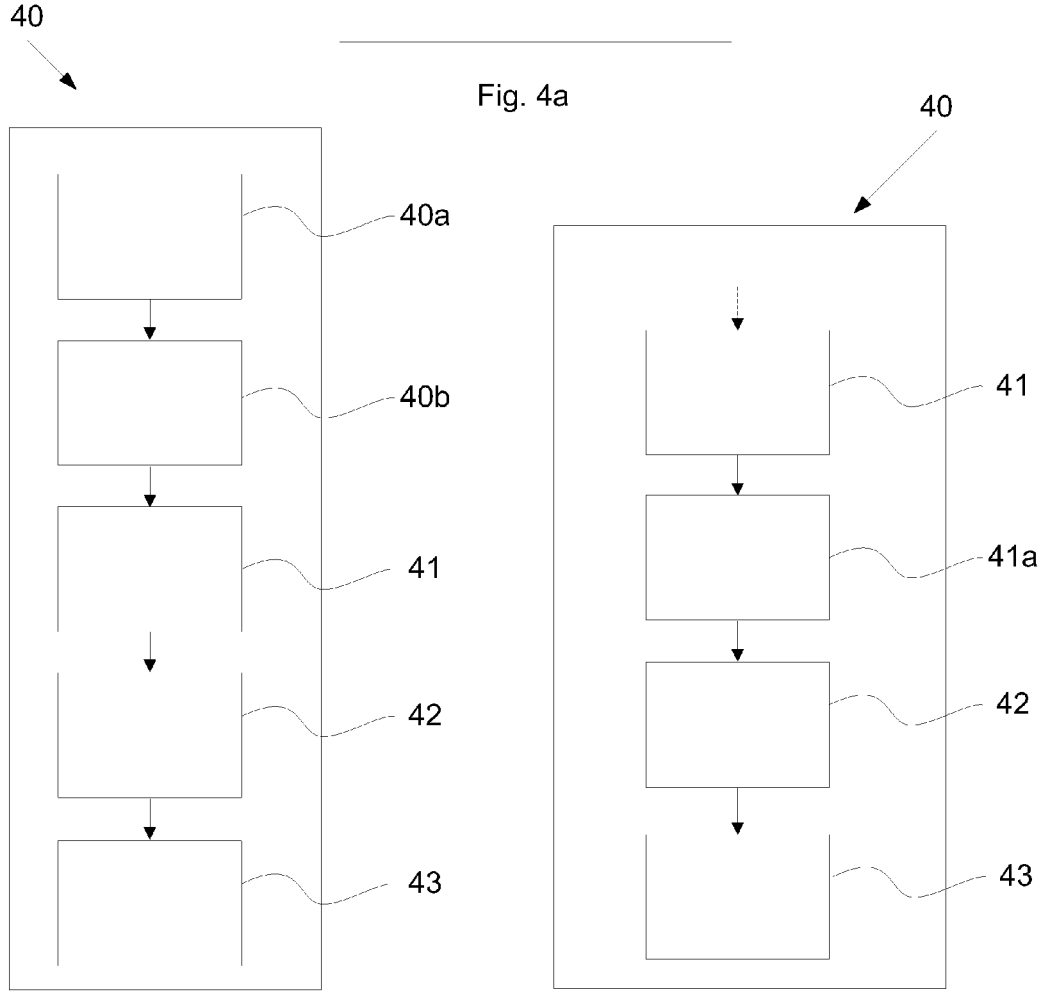

In an embodiment according to FIG. 4b, the method 40, before blocking 41 the user interface, further comprises the steps of displaying 40a precisely one operational touch key 30 and detecting 40b activation of the precisely one operational touch key 30.

Figure 4C:
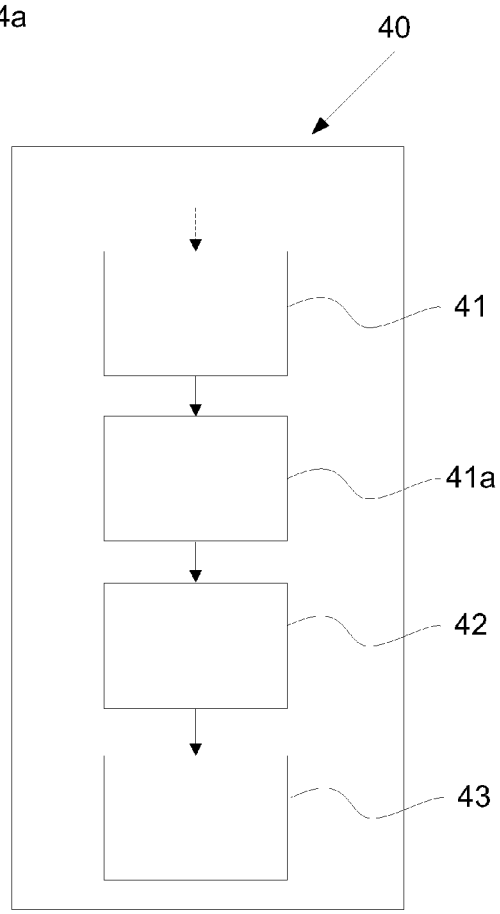

In an embodiment according to FIG. 4c, the method 40, before detecting 42 a first signal from the sensor 108 associated with the critical action, further comprises the step of activating 41a the device 107 for administration of a substance.

Here, the terms "blocking" and "unblocking" the user interface will be explained. The user interface may comprise a first and a second user interface part, where the blocking may affect only the first part, while the second part of the user interface remains open for interaction. Thus, the user is enabled for instance to retrieve and/or configure settings or parameters in the second part while still being prevented to interfere with the critical action associated with the first part. According to one embodiment, the first part of the user interface affects physical parameters connected to the operation of a machine or system while the second part affects abstract parameters, such as presenting instructions, images or other information. According to another embodiment, the first part of the user interface affects a first set of physical parameters connected to the operation of a machine or system and associated with the critical action while the second part of the user interface affects a second set of physical parameters connected to the operation of a machine or system and associated with an action not being related to the critical action associated with the first part of the user interface.

The term "blocking" the user interface means restricting provided selectable alternatives such that a user is only enabled to select a single input, e.g. an emergency stop, or not being enabled to select any input at all. This prohibits a user to interfere with operation at an instant where user interaction may degrade security and/or performance of treatment, and/or where manual/physical actions by the user is required, such as replacing container, duct, syringe, etc., before proceeding. The signal from the sensor(s) confirms that such states of treatment and/or manual/physical actions have been performed correctly. Thereafter, "unblocking" of the user interface can be made, i.e. one operational touch key is enabled such that the user can confirm via the user interface to proceed, while alternatives, e.g. for changing parameters, are still disabled such that the user is strictly guided through the process, such as a treatment or setup.

In an embodiment, where a malfunction is detected the controller is configured to perform "unblocking" of the user interface can be made automatically, and display an alarm related image on the screen, or divert the user interface into a separate critical action pathway. When the cause of malfunctioning has been removed, the controller is configured to automatically return to the previous "blocked" state.

The transition between the blocked and unblocked state, or between a blocked and unblocked state, may be indicated by a sound, a light signal such as a lamp etc. This is advantageous, because it enables a user to be made aware of the transition without having to constantly monitor the screen.

In an embodiment, an interruption touch key 19, such as a cancellation key, is displayed on the touch screen during a preparation procedure to interruption of the current critical action; this may be to provide the user a quick exit from the preparation procedure, for instance due to safety reasons. The controller 22 is further programmed for detecting activation of the cancellation key 19 and unblocks the user interface 21.

In an embodiment, a supplementary key 23 is displayed on the touch screen when being in treatment mode to allow access to alternative operations not being part of the critical operation. The controller is further programmed for detecting activation of the supplementary key 23 and displaying on the screen 16 a supplementary image which in the memory is assigned to the supplementary key. The activation of the supplementary key does not interfere with the critical action such that the probability of error during preparation processes is decreased.

Figure 8:
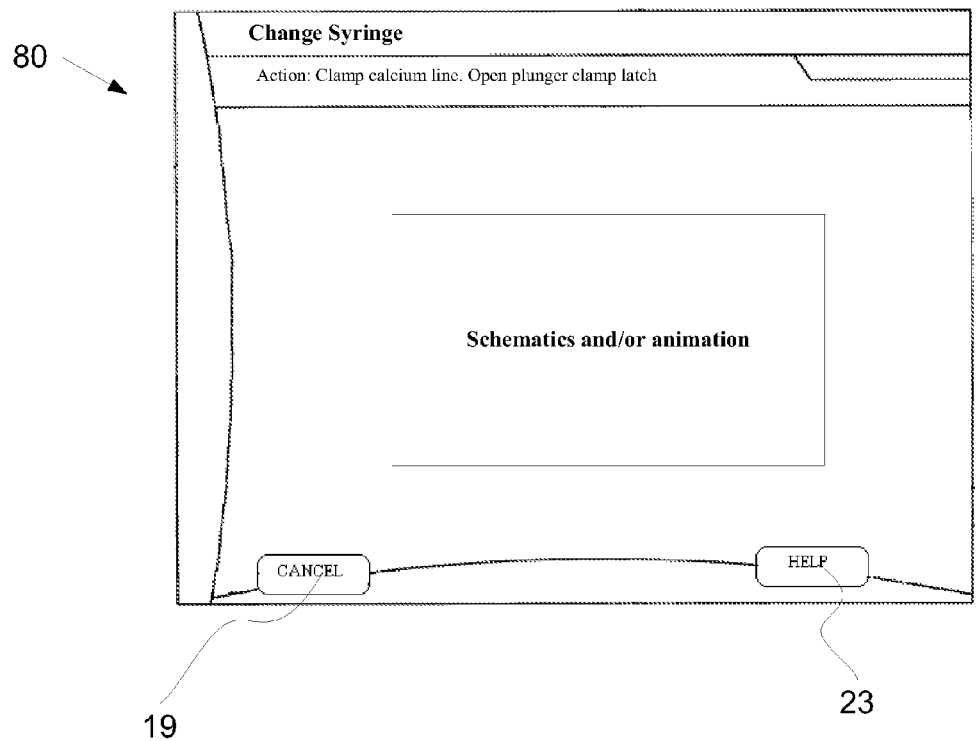
FIG. 8 illustrates a fourth screen view of the user interface during a critical action.

FIG. 8 shows the presence of a cancellation key 19 and a supplementary key 23 according to an embodiment.

Figure 5:
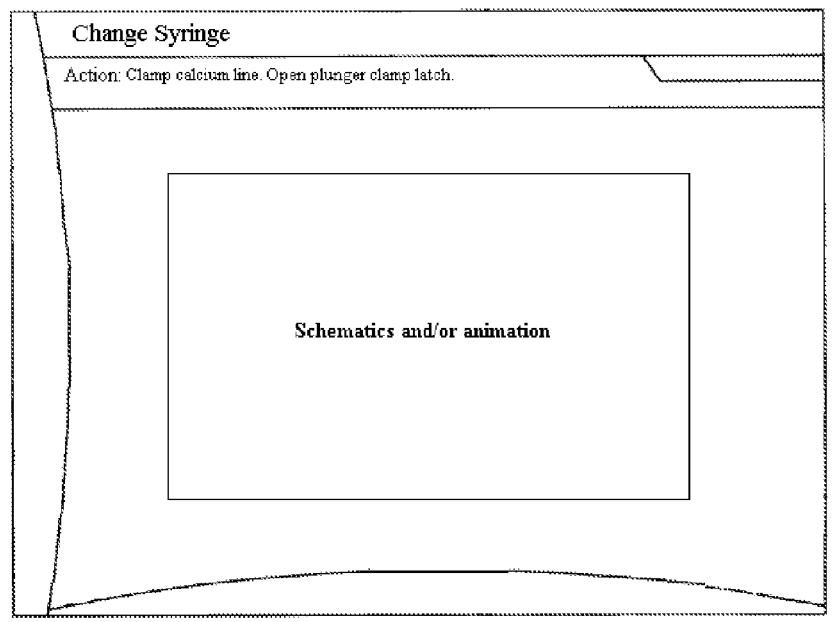
FIG. 5 illustrates a first screen view of the user interface during a critical action.

In an embodiment, an operator of the system 200 activates a touch key 17 denoting "Change Syringe", which is a critical action. The user interface 21 sends an input to the controller that the touch key 17 representing a critical action has been selected. The user interface displays a first image 50 according to FIG. 5, which in a memory of the controller is assigned to the touch key 17. Since the action is critical, the controller 22 then blocks 41 the user interface 21.

The sensor 108 detects 42 when the operator has completed the task of clamping the calcium line and opening the plunger clamp latch, which is the initial task of the "Change Syringe" action, and sends a first signal to the controller. The controller then unblocks 43 the user interface and sends an instruction to the user interface to display a second image 60, according to FIG. 6. The controller also sends an instruction to the user interface to display 40*a* precisely one operational touch key 61.

The user can at this point do nothing else but what is displayed on the screen, since there is only one choice, i.e. according to the precisely one operational touch key 61. When the operator activates the operational touch key 61, the user interface detects 40*b* this and sends a signal to the controller 22. The controller 22 then blocks 46 the user interface 21 and sends a signal to the device 107 for administration of a substance, i.e. a syringe, which is activated 41*a*. Upon activation, the plunger of the syringe is withdrawn.

Figure 7:
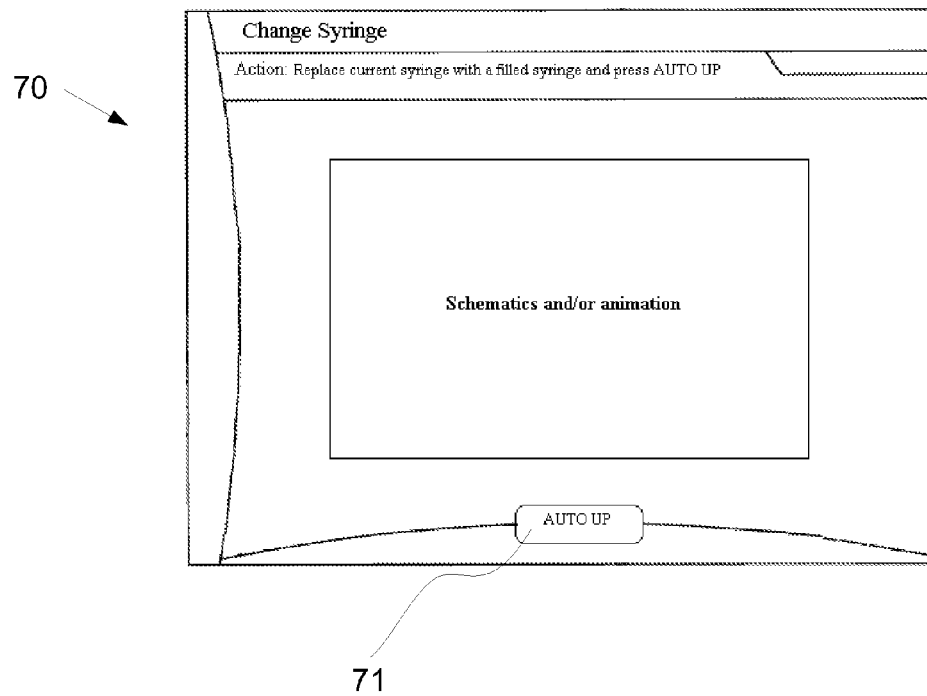
FIG. 7 illustrates a third screen view of the user interface during a critical action.

The sensor 108 detects 48 when the device 107 has completed the critical action, i.e. the plunger is fully withdrawn and sends a second signal to the controller 22. The controller 22 then unblocks 43 the user interface 21 and sends an instruction to the user interface 21 to display a third image 70, according to FIG. 7. In this case, the critical action comprises several steps, and the controller 22 also sends an instruction to the user interface 21 to display precisely one secondary operational touch key 71.

The user replaces the syringe and then continues operation according to the precisely one secondary operational touch key 71. When the operator activates the operational touch key 71, the user interface 21 detects 42 this and sends a signal to the controller 22. The controller 22 then blocks 41 the user interface 21 and sends a signal to the device 107 for administration of a substance, i.e. a syringe, which is activated 41*a*. Upon activation, the plunger of the syringe is inserted.

In an embodiment (not shown), the secondary operational touch key 71 is not displayed until the sensor 108 detects that the syringe has been replaced, i.e. when the operator has completed the critical action.

Thus, there are two general cases of critical actions; one where the machine is the actuator of the critical action, e.g. withdrawing the plunger; and one where the operator is the actuator of the critical action, e.g. replacing the syringe.

The sensor 108 detects 42 when the device 107 has completed the critical action, i.e. the plunger is fully inserted and sends a signal to the controller. The controller unblocks 43 the user interface.

Reference is made to "the sensor 108" in the above demonstrated embodiments for ease of understanding. However, "the sensor 108" can comprise two or more sensors providing signals which by the controller 22 or a combinatory network associated with a set of sensors providing one or more signals to the controller 22 which causes the blocking and unblocking described above. An example is a sensor that can determine type of syringe while another sensor or sensors that can determine position/state of the plunger, etc.

The abovementioned steps may be repeated in any order until the critical action or sequence of critical actions is/are completed and the system returns to the normal operational mode displayed in FIG. 3.

Figure 6:
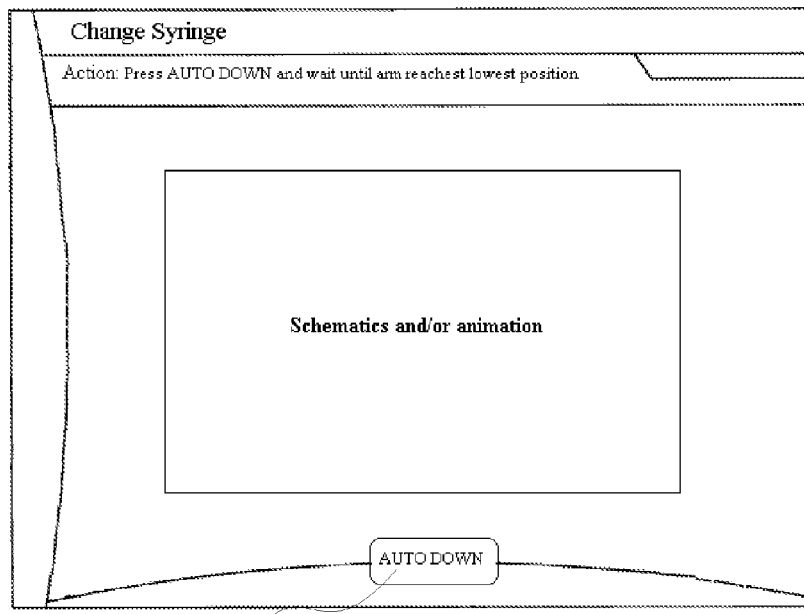
FIG. 6 illustrates a second screen view of the user interface during a critical action.

In an embodiment (not shown), the first image is displayed together with an operational touch key 61, e.g. as depicted in for instance FIG. 6.

In an embodiment, the first 50, second 60 or third 70 image forms part of a video sequence or animation.

In an embodiment the machine comprises units, such as a computer-readable medium, for performing the method according to some embodiments.

In an embodiment the computer-readable medium comprises code segments arranged, when run by an apparatus having computer-processing properties, for performing all of the method steps defined in some embodiments.

The invention may be implemented in any suitable form including hardware, software, firmware or any combination of these. However, preferably, the invention is implemented as computer software running on one or more data processors and/or digital signal processors. The elements and components of an embodiment of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units and processors.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. An extracorporeal blood treatment machine comprising one or more sensors for monitoring a blood treatment device and a user interface for regulating interaction of a user with the blood treatment device according to a predetermined procedure, the predetermined procedure defined by a sequence of one or more critical actions each comprising one or more procedural steps, which user interface comprises at least one screen, at least one memory comprising at least three images, at least a controller, and one or more keys displayable on the at least one screen, wherein the one or more sensors do not detect activation of the one or more keys, wherein the one or more critical actions do not include the user activating the one or more keys, wherein at least one of the one or more sensors is associated with at least one of the one or more critical actions, wherein the one or more critical actions comprise at least one machine critical action being actuated, performed, and completed by the blood treatment device and at least one user critical action being actuated, performed, and completed by the user, and further wherein the controller is programmed to:
   detect activation of a user critical action key of the one or more keys displayed on the at least one screen, wherein the user critical action key is associated with one of the user critical actions;
   display on the screen a first image which in the memory is assigned to the activated user critical action key;
   block the user interface in response to detected activation of the user critical action key until a first signal is received, wherein the first signal is a sensor signal from a sensor of the one or more sensors associated with the one user critical action indicative of the completion of the one user critical action, and further wherein blocking the user interface comprises restricting selectable alternatives of the user interface such that selection through the user interface by the user cannot interfere with completion of the one user critical action;
   upon receipt of the first signal, unblock the user interface and display on the screen a second image and a machine critical action key associated with one of the machine critical actions occurring later in the predetermined procedure than the one user critical action;
   detect activation of the machine critical action key displayed on the at least one screen;
   block the user interface in response to detected activation of the machine critical action key until a second signal is received, wherein the second signal is a sensor signal from a sensor of the one or more sensors associated with the one machine critical action indicative of the completion of the one machine critical action, and further wherein blocking the user interface comprises restricting selectable alternatives of the user interface such that selection through the user interface by the user cannot interfere with completion of the one machine critical action; and
   upon receipt of the second signal, unblock the user interface and display on the screen a third image, wherein the third image corresponds to one or more of the procedural steps occurring later in the predetermined procedure than the one machine critical action.

2. The machine according to claim 1, wherein the controller is further programmed to, before blocking the user interface:
   highlight precisely one operational key as the machine critical action key and allow the user to only select the highlighted precisely one operational key; and
   detect activation of the precisely one operational key before blocking the user interface.

3. The machine according to claim 1, wherein the screen is a touch screen, and further wherein the one or more keys are touch keys.

4. The machine according to claim 1, wherein the first, second or third image forms part of a video sequence.

5. The machine according to claim 1, further comprising a cancellation key,
   and whereupon the controller is further programmed to:
   detect activation of the cancellation key; and
   unblock the user interface.

6. The machine according to claim 1, further comprising a supplementary key,
   and whereupon the controller is further programmed to:
   detect activation of the supplementary key; and display on the screen a supplementary image which in the memory is assigned to the supplementary key.

7. A system for feedback control of a user interface of the machine according to claim 1 comprising a device for performing an operation on a machine for extracorporeal blood treatment, wherein
the controller is configured to receive input from the user interface and send instructions to the user interface;
the controller is configured to control the operation of the device;
the device is monitored by the one or more sensors; and
the controller is configured to receive input from the one or more sensors such that the controller is configured to provide feedback to the user interface by said instructions.

8. The system according to claim 7, wherein the device is configured for administration of a substance, the operation is administration of the substance, and the controller is arranged to control the operation of the device for administration of the substance.

9. The system according to claim 7, wherein the one or more sensors comprise at least one of a load sensor, an optical sensor, a magnetic sensor and an ultrasonic sensor.

10. The machine according to claim 1, wherein the machine further comprises:
at least one blood pump;
at least one housing zone for receiving at least one extracorporeal blood circuit in a position wherein the at least one extracorporeal blood circuit is operatively associated with the blood pump;
at least a machine controller; and
the user interface for dialogue between an operator and the machine controller.

11. The machine according to claim 1, wherein the machine is a dialysis machine.

12. A method for regulating interaction of a user with a blood treatment device in a system for extracorporeal blood treatment according to a predetermined procedure, the predetermined procedure defined by a sequence of one or more critical actions each comprising one or more procedural steps, wherein the system comprises a user interface including a screen and one or more critical action keys displayable on the screen including one or more user critical action keys and one or more machine critical action keys, and further wherein the system comprises one or more sensors for monitoring the blood treatment device and associated with the one or more critical actions, wherein the one or more sensors do not detect activation of any of the one or more critical action keys, wherein the one or more critical actions do not include the user activating the one or more critical action keys, wherein the one or more critical actions comprise at least one machine critical action being actuated, performed, and completed by the blood treatment device and at least one user critical action being actuated, performed, and completed by the user, said method comprising:
detecting activation of a user critical action key displayed on the at least one screen, wherein the user critical action key is associated with one of the user critical actions;
displaying on the screen a first image corresponding to the activated user critical action key;
blocking the user interface in response to detected activation of the user critical action key until a first signal is received, wherein the first signal is a sensor signal from a sensor of the one or more sensors associated with the one user critical action indicative of the completion of the one user critical action, wherein blocking the user interface comprises restricting selectable alternatives of the user interface such that selection through the user interface by the user cannot interfere with the completion of the one user critical action;
detecting the first signal from the sensor associated with the one user critical action;
unblocking the user interface when the first signal is detected and displaying on the screen a second image and a machine critical action key associated with one of the machine critical actions occurring later in the predetermined procedure than the one user critical action;
detecting activation of the machine critical action key displayed on the at least one screen;
blocking the user interface in response to detected activation of the machine critical action key until a second signal is received, wherein the second signal is a sensor signal from a sensor of the one or more sensors associated with the one machine critical action indicative of the completion of the one machine critical action, and further wherein blocking the user interface comprises restricting selectable alternatives of the user interface such that selection through the user interface by the user cannot interfere with completion of the one machine critical action;
detecting the second signal from the sensor associated with the one machine critical action; and
unblocking the user interface when the second signal is detected and displaying on the screen a third image, wherein the third image corresponds to one or more of the procedural steps occurring later in the predetermined procedure than the one machine critical action.

13. The method according to claim 12, wherein, upon unblocking the user interface when the first signal is detected, the method further comprises:
highlighting precisely one operational key as the machine critical action key and allowing the user to only select the highlighted precisely one operational key; and
detecting activation of the precisely one operational key.

14. The method according to claim 12, wherein one of the one or more sensors is associated with a device configured to administrate a substance, and wherein the method further comprises, before detecting the first signal from the sensor associated with the one user critical action:
activating the device for administration of the substance.

15. An extracorporeal blood treatment machine comprising one or more sensors, a syringe interface apparatus configured to receive a syringe apparatus for administration of a substance monitored by the one or more sensors, and a user interface for regulating interaction of a user with the syringe interface apparatus and the syringe apparatus according to a predetermined procedure for changing the syringe apparatus, the predetermined procedure defined by a sequence of one or more critical actions each comprising one or more procedural steps, which user interface comprises at least one screen, at least one memory comprising at least three images, at least a controller and one or more keys displayable on the at least one screen, wherein at least one of the one or more sensors is associated with at least one of one or more critical actions, wherein the one or more sensors do not detect activation of the one or more keys, wherein the one or more critical actions do not include the user activating the one or more keys, wherein the one or more critical actions
detect activation of the machine critical action key displayed on the at least one screen;

block the user interface in response to detected activation of the machine critical action key until a second signal is received, wherein the second signal is a sensor signal from a sensor of the one or more sensors associated with the one machine critical action indicative of the completion of the one machine critical action comprising withdrawal of the plunger of the syringe apparatus, and further wherein blocking the user interface comprises restricting selectable alternatives of the user interface such that selection through the user interface by the user cannot interfere with completion of the one machine critical action; and upon receipt of the second signal, unblock the user interface and display on the screen a third image, wherein the third image corresponds to one or more of the procedural steps occurring later in the predetermined procedure than the one machine critical action.

16. The machine according to claim 15, wherein the controller is further programmed to:

highlight precisely one operational key as the machine critical action key and allow the user to only select the highlighted precisely one operational key; and comprise at least one machine critical action being actuated, performed, and completed by the syringe interface apparatus and at least one user critical action being actuated, performed, and completed by the user, and further wherein the controller is programmed to:

detect activation of a user critical action key of the one or more keys displayed on the at least one screen associated with one of the user critical actions comprising the user preparing the syringe interface apparatus for removal of the syringe apparatus;

display on the screen a first image which in the memory is assigned to the activated user critical action key;

block the user interface in response to detected activation of the user critical action key until a first signal is received, wherein the first signal is a sensor signal from a sensor of the one or more sensors associated with the one user critical action indicative of the user completing the one user critical action comprising preparing the syringe interface apparatus for removal of the syringe apparatus, and further wherein blocking the user interface comprises restricting selectable alternatives of the user interface such that selection through the user interface by the user cannot interfere with completion of the one user critical action;

upon receipt of the first signal, unblock the user interface and display on the screen a second image and a machine critical action key associated with one of the machine critical actions comprising withdrawing a plunger of the syringe apparatus and occurring later in the predetermined procedure than the one user critical action;

detect activation of the precisely one operational key before blocking the user interface.

17. The machine according to claim 16, wherein the screen is a touch screen, and further wherein the one or more keys are touch keys.

* * * * *

UNITED STATES PATENT AND TRADEMARK OFFICE
CERTIFICATE OF CORRECTION

PATENT NO.          : 9,514,322 B2                                    Page 1 of 1
APPLICATION NO.     : 13/583726
DATED               : December 6, 2016
INVENTOR(S)         : Arash Golshenas It is certified that error appears in the above-identified patent and that said Letters Patent is hereby corrected as shown below:

In the Claims

Claim 15, Column 16, Line 65, after the word "actions" please add --comprise at least one machine critical action being actuated, performed, and completed by the syringe interface apparatus and at least one user critical action being actuated, performed, and completed by the user, and further wherein the controller is programmed to:
    detect activation of a user critical action key of the one or more keys displayed on the at least one screen associated with one of the user critical actions comprising the user preparing the syringe interface apparatus for removal of the syringe apparatus;
    display on the screen a first image which in the memory is assigned to the activated user critical action key;
    block the user interface in response to detected activation of the user critical action key until a first signal is received, wherein the first signal is a sensor signal from a sensor of the one or more sensors associated with the one user critical action indicative of the user completing the one user critical action comprising preparing the syringe interface apparatus for removal of the syringe apparatus, and further wherein blocking the user interface comprises restricting selectable alternatives of the user interface such that selection through the user interface by the user cannot interfere with completion of the one user critical action upon receipt of the first signal, unblock the user interface and display on the screen a second image and a machine critical action key associated with one of the machine critical actions comprising withdrawing a plunger of the syringe apparatus and occurring later in the predetermined procedure than the one user critical actions;--.

Claim 16, Column 17, Line 22, please delete "com-".

Claim 16, Column 17, please delete Lines 23 through 30.

Claim 16, Column 18, please delete Lines 1 through 23.

Signed and Sealed this
Fourth Day of April, 2017

Michelle K. Lee
*Director of the United States Patent and Trademark Office*